United States Patent [19]

Avolio

[11] 4,381,766

[45] May 3, 1983

[54] BACK APPLICATOR

[76] Inventor: Anita M. Avolio, 214 Bull Run Rd., Trenton, N.J. 08638

[21] Appl. No.: 188,958

[22] Filed: Sep. 19, 1980

[51] Int. Cl.³ .................... A61H 7/00; A61M 35/00
[52] U.S. Cl. ............................ 128/62 R; 15/143 R; 604/289
[58] Field of Search .................. 128/62 R, 269, 357, 128/365, 393, DIG. 15; 132/88.5, 88.7; 15/143 R, 144 R, 244 A; 401/6, 268

[56] References Cited

U.S. PATENT DOCUMENTS

| | | | |
|---|---|---|---|
| 1,504,641 | 8/1924 | Mukai | 15/143 R |
| 2,168,975 | 8/1939 | Clarke | 128/62 |
| 2,446,401 | 8/1948 | Ziskind | 15/144 R |
| 3,103,682 | 9/1963 | Markle | 128/269 |
| 3,346,904 | 10/1967 | Armstrong | 128/DIG. 15 |
| 3,568,237 | 3/1971 | Rhodes | 15/244 A |
| 3,618,596 | 11/1971 | Miller | 128/62 |

*Primary Examiner*—C. Fred Rosenbaum

[57] ABSTRACT

The back applicator is used to apply lotions, creams, oils, and other soothing and medicating substances to the back area where it is difficult to reach. By simply applying your favorite lotion onto the pad, it can be evenly distributed over the body.

The applicator pad can be easily removed for cleaning or replacement purposes to provide for maximum cleanliness and health reasons. The applicator is equipped with a free-floating pad which will conform to the back as you slide it gently and smoothly over your skin. The pad is made of resilient absorbant material and is attached to the pad housing by a quick grasp of the Velcro fabric, therefore, making it easy to remove. The pad can be cleaned simply with soap and water. After it becomes worn, new pads can be purchased. The knurled surface of the handle allows the user to secure a good grip.

2 Claims, 3 Drawing Figures

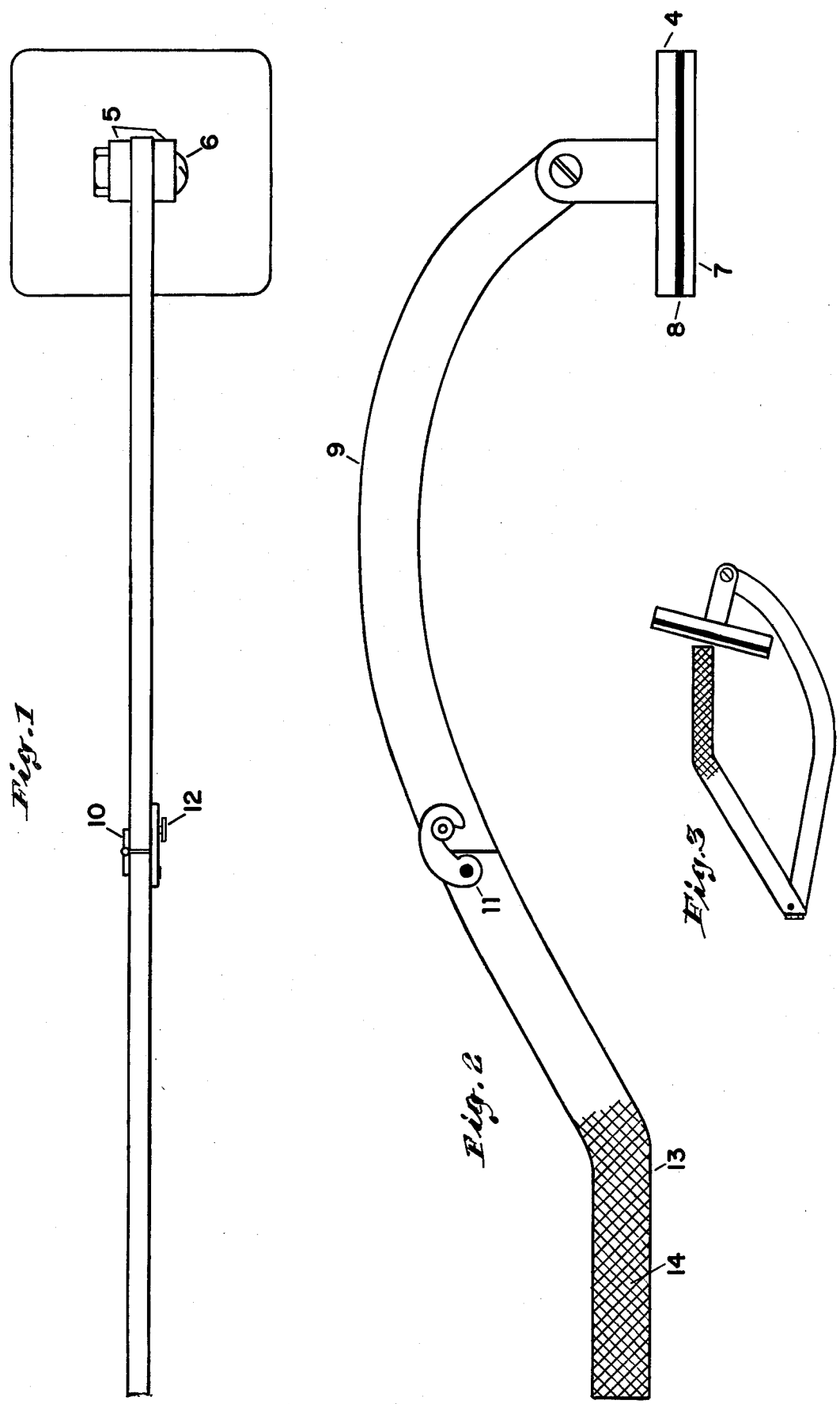

BACK APPLICATOR

The back applicator that I have designed consists of the following details. The pad housing is located at the pad end of the applicator. Perpendicular to the pad housing are two pieces far enough apart and tall enough to allow the arm to be placed between them. A bolt with nut is inserted through all three pieces making the pad housing free-floating.

On the underneath side of the pad housing is the pad. It is made of resilient absorbant material and is attached to the pad housing by a quick grasp of the Velcro fabric. The pads are removable and can be replaced.

The arched shape of the arm gives the user more distance in which to reach their back. The hinge is located on one side of the handle. Opposite the hinge is the latch. The latch, attached by a pivot, swings down and friction fits over a small headed pin which extends perpendicular to the arm in front of the latch. The latch locks the hinge enabling the back applicator to be ready for use. This locking feature prohibits the applicator from closing while in use.

The handle, which is a continuation of the arm, is a straight knurled piece giving the user a secure grip.

The applicator can be collapsed. This makes it very convenient for traveling and storing purposes.

DRAWINGS

FIG. 1 is a top plan view of the present invention.

FIG. 2 is a perspective view of the apparatus comprising a typical embodiment of the present invention.

FIG. 3 is a side view of the present invention as seen when it is collapsed.

DETAILS

Referring to FIGS. 1-3, the pad housing (4), is located at the pad end of the applicator. Perpendicular to the pad housing (4) are two pieces (5) separated by the thickness of the arm and tall enough to allow the arm to swing. A bolt with nut (6) is inserted through all three pieces making the pad housing (4) free-floating.

On the underneath side of the pad housing is the pad (7). It is made of resilient absorbant material and is attached to the pad housing (4) by a quick grasp of the Velcro fabric (8). The pads (7) are removable and can be replaced.

The arched shape (9) of the arm gives the user more distance in which to reach their back. The hinge (10), is located on one side of the handle. Opposite the hinge is the latch (11). The latch, attached by a pivot (12), swings down and friction fits over a small headed pin (13) which extends perpendicular to the arm in front of the latch (11). The latch locks the hinge enabling the back applicator to be ready for use. This locking feature prohibits the applicator from closing while in use.

The handle (14), a continuation of the arm (9), is a straight knurled piece (15), giving the user a secure grip.

The applicator can be collapsed as shown in FIG. 3. This makes it very convenient for traveling and storing.

I claim:

1. An applicator for applying lotions to portions of the body that are difficult to reach comprising: an elongated handle which is bilaterally symmetrical about one plane, having a proximal portion adapted to be grasped by an operator's hand, and a curved distal portion which extends from the proximal portion and terminates at an applicator end; a pad housing connected to said applicator end of the distal portion of the handle; a fastening means attached to the pad housing; said fastening means comprising one of a first and second element, said first element comprising a series of hooks, said second element comprising a series of loops; said handle comprising two parts which are pivotally connected to fold about an axis which is parallel to said plane and including means for releasably locking the two parts in aligned relationship.

2. An applicator as claimed in claim 1 wherein the proximal portion extends over approximately one-fifth of the handle's length to form an elongated straight handle portion and wherein the applicator end terminates in general alignment with the longitudinal axis of the proximal portion.

* * * * *

UNITED STATES PATENT AND TRADEMARK OFFICE
CERTIFICATE OF CORRECTION

PATENT NO. : 4,381,766

DATED : May 3, 1983

INVENTOR(S) : Anita M. Avolio

Page 1 of 3

It is certified that error appears in the above-identified patent and that said Letters Patent is hereby corrected as shown below:

The title page and Figs. 1 and 2 of the drawings should appear as shown on the attached sheets.

Signed and Sealed this

Third Day of July 1984

[SEAL]

Attest:

Attesting Officer

GERALD J. MOSSINGHOFF

Commissioner of Patents and Trademarks

United States Patent [19]

Avolio

[11] 4,381,766
[45] May 3, 1983

[54] BACK APPLICATOR

[76] Inventor: Anita M. Avolio, 214 Bull Run Rd., Trenton, N.J. 08638

[21] Appl. No.: 188,958

[22] Filed: Sep. 19, 1980

[51] Int. Cl.³ .................... A61H 7/00; A61M 35/00
[52] U.S. Cl. ........................ 128/62 R; 15/143 R; 604/289
[58] Field of Search .............. 128/62 R, 269, 357, 128/365, 393, DIG. 15; 132/88.5, 88.7; 15/143 R, 144 R, 244 A; 401/6, 268

[56] References Cited

U.S. PATENT DOCUMENTS

| 1,504,641 | 8/1924 | Mukai | 15/143 R |
| 2,168,975 | 8/1939 | Clarke | 128/62 |
| 2,446,401 | 8/1948 | Ziskind | 15/144 R |
| 3,103,682 | 9/1963 | Markle | 128/269 |
| 3,346,904 | 10/1967 | Armstrong | 128/DIG. 15 |
| 3,568,237 | 3/1971 | Rhodes | 15/244 A |
| 3,618,596 | 11/1971 | Miller | 128/62 |

Primary Examiner—C. Fred Rosenbaum

[57] ABSTRACT

The back applicator is used to apply lotions, creams, oils, and other soothing and medicating substances to the back area where it is difficult to reach. By simply applying your favorite lotion onto the pad, it can be evenly distributed over the body.

The applicator pad can be easily removed for cleaning or replacement purposes to provide for maximum cleanliness and health reasons. The applicator is equipped with a free-floating pad which will conform to the back as you slide it gently and smoothly over your skin. The pad is made of resilient absorbant material and is attached to the pad housing by a quick grasp of the Velcro fabric, therefore, making it easy to remove. The pad can be cleaned simply with soap and water. After it becomes worn, new pads can be purchased. The knurled surface of the handle allows the user to secure a good grip.

2 Claims, 3 Drawing Figures

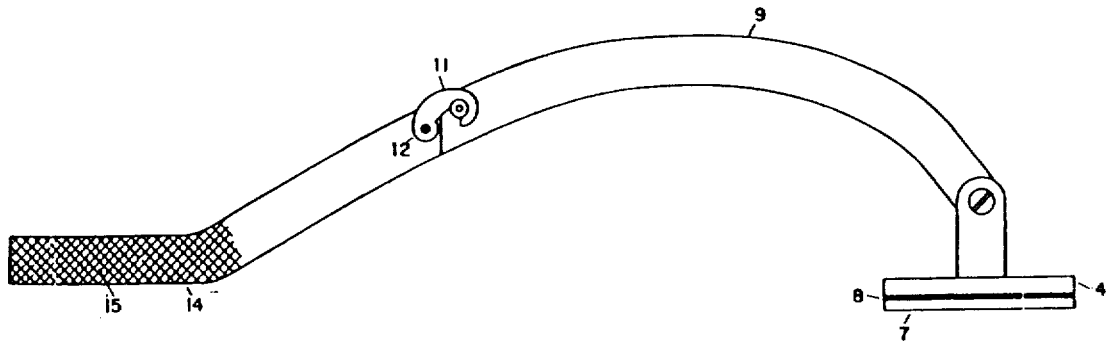

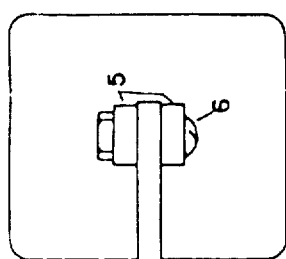
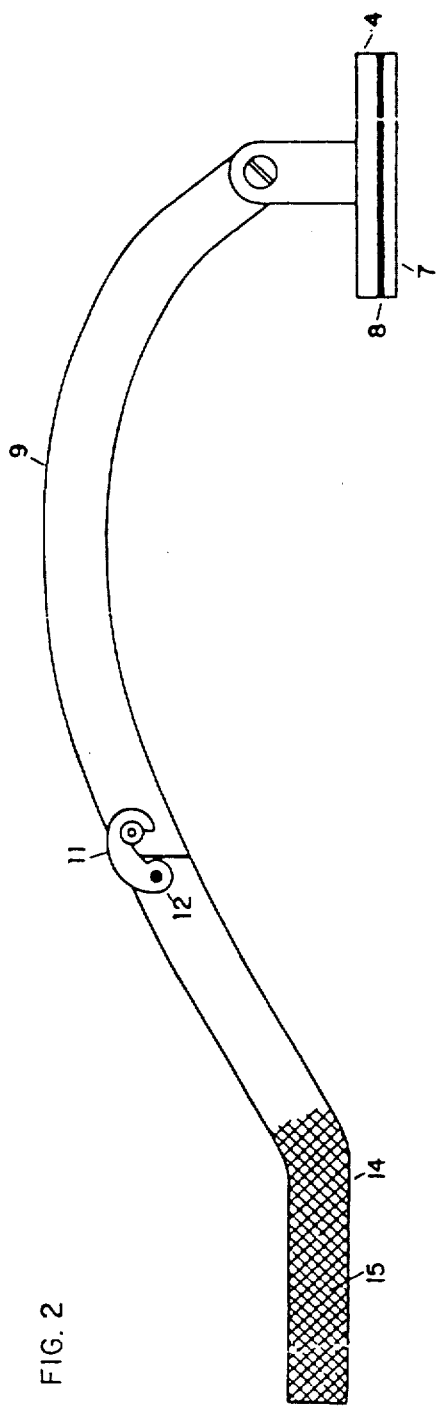
FIG. 1
FIG. 2